United States Patent [19]

Kelley

[11] Patent Number: 5,756,113
[45] Date of Patent: May 26, 1998

[54] LIQUID FORMULATIONS CONTAINING FLUORINATED ACRYLIC COPOLYMER

[76] Inventor: Donald W. Kelley, 608 N. Palestine, Athens, Tex. 75751

[21] Appl. No.: 893,662

[22] Filed: Jun. 5, 1992

Related U.S. Application Data

[63] Continuation-in-part of Ser. No. 670,306, Mar. 15, 1991, abandoned.

[51] Int. Cl.$^6$ .............................. A01N 37/14; A01N 37/16
[52] U.S. Cl. .................... 424/405; 424/409; 424/410; 424/411; 424/59; 424/78.05; 424/78.02; 424/78.08; 424/DIG. 10; 424/70.9; 424/70.1; 514/919; 514/920; 514/937
[58] Field of Search .................... 424/405, 409, 424/411, 410, 59, 78.05, 78.02, 78.08, DIG. 10, 70.9, 70.1; 514/937, 919, 920

[56] References Cited

U.S. PATENT DOCUMENTS

| 4,478,975 | 10/1984 | Dessaint et al. | 528/53 |
| 4,778,915 | 10/1988 | Lina et al. | 526/242 |
| 4,983,390 | 1/1991 | Levy | 424/409 |

*Primary Examiner*—Raj Bawa
*Attorney, Agent, or Firm*—Donald W. Erickson

[57] ABSTRACT

Active ingredient containing liquid formulations wherein the active ingredient is made water and oil resistant after application thereof to a substrate by the addition to the formulation of a fluorinated acrylic copolymer. The substrate can be either an animate or inanimate object. Active ingredients include repellents, attractants, pesticides, growth regulators, sunscreen agents, or medicines. The liquid formulations can be aqueous or organic solvent based or a mixture thereof.

20 Claims, No Drawings

LIQUID FORMULATIONS CONTAINING FLUORINATED ACRYLIC COPOLYMER

This is a continuation-in-part of Ser. No. 07/670,306, filed Mar. 15, 1991, now abandoned, the disclosure of which is incorporated herein.

BACKGROUND OF THE INVENTION

This invention relates to liquid compositions characterized by increased or extended efficacy of the active ingredient therein, even though the active ingredient is exposed to water and/or oil after application thereof to a substrate.

Active ingredient formulations such as herbicidal or insecticidal formulations which utilize water are traditionally formulated with emulsifiers. These emulsifiers are surface active agents which remain with the active ingredient after the formulation has been applied to a substrate and dried. When water, e.g. rain, comes into contact with the applied formulation, it is subject to re-emulsification and ready removal or dilution of the active ingredient from the substrate. It is obvious that as the active ingredient is removed, in whole or in part, by water contact that the intended benefit of the active ingredient is eliminated or reduced. Thus, it is common on many product labels and inserts of active ingredient formulations such as herbicide formulations, insecticide formulations, sunscreen formulations, etc. to find a cautionary statement that if the formulation is contacted by or exposed to water within 2, 12, 24 or 48 hours, or the like, after application, then reduced efficacy or effectiveness can be expected and the formulation should be reapplied. Similarly, hydrophobic materials such as oils, fatty acids, sebum, etc. can solublize the active ingredient of formulations such as insect repellent and insecticide formulations as they come in contact with each other. Thus, the active ingredient can be removed, in whole or in part, from the substrate, thereby eliminating or reducing the effectiveness of the active ingredient. The present invention inhibits the removal of active ingredients from formulations by water or oil contact after application thereof to a substrate. This invention, therefore, eliminates or significantly reduces the need for re-application of active ingredient formulations.

SUMMARY OF THE INVENTION

The present invention is directed at an active ingredient containing liquid formulation which contains a fluorinated acrylic copolymer in an amount effective to make the active ingredient(s) resistant to removal or dilution by water or oil after application thereof to a substrate. Flourinated acrylic copolymers useful in the present invention are exemplified by the fluoroacroxylic copolymers supplied by Atochem under the product name Foraperle such as Foraperle B208, 300 and 303.

The improved formulations of the present invention can be used on substrates such as humans, small and large animals, vegetation, wood surfaces, traps, baits, etc. Biologically active ingredients containing liquid formulations of this invention include formulations in which the active ingredient is a repellent, an attractant, a pesticide, a growth regulator, a sunscreen agent, a medicinal, etc. The active ingredient liquid formulations of this invention can be water-based or organic solvent-based.

The fluorinated acrylic copolymers useful in the water and oil resistant formulations of the present invention include copolymers prepared by the polymerization of a perfluoroalkyl acrylate monomer of formula I and an acrylate monomer of formula II:

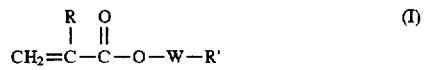

wherein R is hydrogen or a lower alkyl of 1 to 4 carbon atoms, W is an alkylene of 1 to 6 carbon atoms, R' is a perfluoroalkyl of 2 to 20 carbon atoms and R" is lower alkyl of 1 to 6 carbon atoms, hydroxyalkylene of 2 to 4 carbon atoms or the group $-(CH_2)n-NH-R'''$ in which R''' is lower alkyl of 1 to 6 carbon atoms or cycloalkyl and n is an integer of 2 to 4.

The term "alkyl" includes straight and branched chain alkyl groups.

The term "cycloalkyl" means a cycloalkyl hydrocarbon of 4 to 8 carbon atoms.

The fluorinated acrylic copolymers can be prepared by polymerization such as emulsion polymerization using standard procedures such as described in U.S. Pat. Nos. 4,478,975 and 4,778,915, the disclosures of which are incorporated herein by reference. The copolymers are prepared using about 1 to 30 percent of a monomer of formula II, more usually 1 to 10 percent, based on the total weight of monomers I and II.

The amount of fluorinated acrylic copolymer included in an active ingredient liquid formulation to make the active ingredient, water and oil resistant may vary from one formulation to the next. The most effective amount of fluorinated acrylic copolymer can be easily determined by routine testing. Generally, the fluorinated acrylic copolymer will be present in the liquid formulation within the range of about 1 to 20 percent by weight of the total formulation, more usually, 2 to 10 percent.

DETAILED DESCRIPTION OF THE INVENTION

The following examples are provided to illustrate the practice of the present invention.

Example 1

The following active ingredient liquid formulations (animal insect repellent spray) were prepared and tested on large long haired Labrador Retrievers.

| Formulation 1 | |
|---|---|
| Ingredients | Percentage |
| 1. Water | 89.008 |
| 2. Carbopol 1342* | .150 |
| 3. Ammonium Hydroxide 28% | .075 |
| 4. Cypermethrin 90% | .167 |
| 5. Pyrethrins 20% | 1.000 |
| 6. Piperonyl Butoxide Tech. | 1.600 |
| 7. MKG 326** | .500 |
| 8. MKG 11** | .500 |
| 9. Stabilene** 100% | 5.000 |
| 10. Foraperle 300*** | 2.0 |

*Crosslinked polymer of acrylic acid of B. F Goodrich Co.
**Insect repellents of McLaughlin, Gormley King Co. and Union Carbide.
***Fluorinated acrylic copolymer of Atochem, Inc.

Formulation 2 is the same as Formulation 1 with the exception that ingredient 10, the fluorinated copolymer, was omitted.

Formulation Procedure:
1. Charge mixing vessel with ingredient 1 and adjust mixer until a vortex is created.
2. Sift ingredient 2 into vortex of ingredient 1. When ingredient 2 has been wet out, slow mixer to allow trapped air to escape and ingredient 2 to hydrolyze.
3. Add ingredient 3 and disperse completely.
4. Turn mixer up so as to pull a vortex, then add preblended ingredients 4 through 9 to make the emulsion. Reduce mixer speed but allow to mix until smooth.
5. Add ingredient 10 and mix until uniform.
6. Adjust pH to 6.0±.2.

The practicality of and effectiveness of the animal insect repellent spray of Formulation 1 (in accordance with the present invention) was evaluated by treating two large long haired Labrador Retrievers with Formulation 1. The spray was applied to each animal's entire coat and allowed to dry.

Prior to treatment, the animals had extremely high mosquito counts (50–100) and they were penned in an environment with extremely high mosquito pressure.

To evaluate the water and oil proofing properties of Formulation 1, the animals were allowed to swim in a nearby creek every other day and were subjected to rain (sprinkling) on a frequent basis.

Observations were made each day with the following result. Formulation 1 was effective in maintaining the animals mosquito free for thirty days. The repellency started declining within the next five days and was ineffective by 35 days.

When the animals again had high counts of mosquitoes on their coat (50–100) they were sprayed with Formulation 2. The same procedure was followed for this evaluation as for the first. Formulation 2 was effective in maintaining the animals mosquito free for four days and was ineffective at the end of seven days.

Example 2

A premis spray was made and evaluated for water resistance as follows:

Formulation 3

| Ingredients | Percentage |
|---|---|
| 1. DI Water | 93.275 |
| 2. Carbopol 1342 | .150 |
| 3. Ammonium Hydroxide | .075 |
| 4. Permethrin | .500 |
| 5. Piperonyl Butoxide | 2.500 |
| 6. Diazinon | .500 |
| 7. Foraperle 303* | 3.000 |

*Fluorinated acrylic copolymer of Atochem, Inc.

Formulation 4 was made the same as Formulation 3 except that ingredient 7 was omitted.

The same formulation or mixing procedure was used as in Example 1.

1. Six microscope slides were dipped into each of Formulation 3 and 4, allowed to dry 24 hours and weighed.
2. The slides were then placed identically under a stream of water with a steady flow and rinsed for 30, 90 and 300 seconds. The slides were then allowed to air dry for one hour.
3. Each slide was weighed and the amount of premis spray removed by rinsing calculated.

Results

| Formulation 3 | Slide 1 | 2 | 3 | 4 | 5 | 6 |
|---|---|---|---|---|---|---|
| Treated Slide | 4.52 | 4.36 | 4.37 | 4.41 | 4.37 | 4.44 |
| Untreated Slide | 4.50 | 4.35 | 4.36 | 4.39 | 4.36 | 4.43 |
| Add On | .02 | .01 | .01 | .02 | .01 | .01 |
| 30 Sec. Rinse | 4.52 | 4.36 | 4.37 | — | — | — |
| Percent Loss | (0%) | (0%) | (0%) | — | — | — |
| 90 Sec. Rinse | — | — | — | 4.41 | 4.37 | 4.44 |
| Percent Loss | — | — | — | (0%) | (0%) | (0%) |
| 300 Sec. Rinse | 4.51 | 4.36 | 4.37 | — | — | — |
| Percent Loss | (50%) | (0%) | (0%) | — | — | — |

| Formulation 4 | Slide 7 | 8 | 9 | 10 | 11 | 12 |
|---|---|---|---|---|---|---|
| Treated Slide | 4.48 | 4.46 | 4.47 | 4.48 | 4.51 | 4.48 |
| Untreated Slide | 4.47 | 4.45 | 4.46 | 4.47 | 4.50 | 4.47 |
| Add On | .01 | .01 | .01 | .01 | .01 | .01 |
| 30 Sec. Rinse | 4.47 | 4.45 | 4.46 | — | — | — |
| Percent Loss | (100%) | (100%) | (100%) | — | — | — |
| 90 Sec. Rinse | — | — | — | 4.47 | 4.50 | 4.47 |
| Percent Loss | — | — | — | (100%) | (100%) | (100%) |

Example 3

It is well known than an animal's body produces oils in the form of sebum which readily travel up the hair shafts found on the animal's body. These oils will act as diluents for the active ingredients and spread them over a larger surface area reducing their availability and dose levels. They also act as a release agent for the actives and allow them to be easily removed from the hair by the animal coming into contact with other substrates, such as the ground, bedding, etc.

The fluorinated acrylic copolymers used in the present invention when applied with active ingredients render them and the hair shaft hydro as well as lipophobic preventing the sebum from migrating up the hair shaft and diluting or displacing the active ingredients. To demonstrate this phenomena, the following comparison was made: A pyrethrin/PBO spray with and without a fluorinated acrylic copolymer was applied to three each beagles. The beagles were not bathed and were prevented from coming in contact with water other than drinking.

Formulation 5

| Ingredients | Percentage |
|---|---|
| Isopropyl alcohol | 30.00 |
| DI Water | 44.58 |
| Carbopol 1342 | .15 |
| Ammonium Hydroxide | .03 |
| Pyrethrin 50% | 2.00 |
| Piperonyl Butoxide | 3.74 |
| Foraperle 303 | 19.50 |

The formulation was diluted at the ratio of 1 part Formulation 5 to 5.5 parts water prior to application to the animals.

Formulation 6 was the same as Formulation 5 except that Foroperle 303 was omitted. It also was diluted as above before application.

Results

The total number of fleas and ticks found on three beagles which were infested with 100 fleas and 50 ticks 4 days pretreatment, and 2, 4, 8, 10, 13, and 20 days post treatment.

| Treatment | Days | | | | | | | | | | |
|---|---|---|---|---|---|---|---|---|---|---|---|
| | 0 | 1 | 2 | 3 | 4 | 7 | 9 | 10 | 11 | 14 | 21 |
| Fleas | | | | | | | | | | | |
| Formulation 5 | 83 | 0 | 0 | 0 | 0 | 0 | 5 | 3 | 24 | 13 | 16 |
| Formulation 6 | 85 | 5 | 0 | 1 | 0 | 5 | 34 | 27 | 87 | 75 | — |
| Untreated | 71 | 53 | 97 | 89 | 87 | 132 | 93 | 75 | 111 | 72 | 63 |
| Ticks | | | | | | | | | | | |
| Formulation 5 | 34 | 11 | 0 | 0 | 0 | 1 | 5 | 5 | 42 | 34 | 38 |
| Formulation 6 | 50 | 25 | 7 | 14 | 7 | 37 | 29 | 28 | 76 | 71 | — |
| Untreated | 42 | 41 | 39 | 56 | 54 | 67 | 65 | 64 | 87 | 82 | 54 |

Example 4

A sunscreen formula with and without a fluorinated acrylic copolymer was made and tested along with a commercially available waterproof sunscreen known as Bull Frog by Chattem, Inc. Each formulation was applied to strips of blotter paper and allowed to dry overnight. Drops of water were applied to each paper. The commercial product (Bull Frog) as well as the formula without the fluorinated acrylic copolymer absorbed the water whereas the formula with the fluorinated acrylic copolymer (Foraperle 303) stood the water up in droplets and did not allow it to penetrate the paper.

The formulas were as follows:

| | Percentages | |
|---|---|---|
| $DIH_2O$ | 77.85 | 80.85 |
| Carbopol 1342 | .5 | .5 |
| Octyl Methoxycinnamate | 7.5 | 7.5 |
| Oxybenzone | 6.0 | 6.0 |
| Octyl Salicylate | 5.0 | 5.0 |
| TEA (Triethanol amine) | .15 | .15 |
| Foraperle 303 | 3.00 | — |

Example 5

The following Formulation 7 was made and tested on large animals as a pour-on.

Formulation 7

| Ingredients | Percentage |
|---|---|
| Isopropyl alcohol | 30.00 |
| DI Water | 65.82 |
| Carbopol 1342 | .15 |
| Ammonium Hydroxide | .03 |
| Permethrin | 1.00 |
| Foraperle 303 | 3.00 |

Formulation 7 was compared with a one percent permethrin pour on product known as DeLice by Durvet, Inc. which does not contain any fluorinated acrylic copolymer (Formulation 8). Three ounces of each formulation were applied to five head of cattle each. The following data show the average number of horn flies found on the cattle and the percent reduction corrected using Abbotts Formula (control minus treatment divided by control times 100).

| | The Average Number of Horn Flies Found on 5 Head of Cattle | | |
|---|---|---|---|
| Days | Formulation 8 | Formulation 7 | Untreated Controls |
| 0 | 840.0 | 940.0 | 800 |
| 1 | 3.0 | 4.5 | 815 |
| 7 | 6.5 | 6.0 | 920 |
| 14 | 7.5 | 3.5 | 850 |
| 21 | 25.5 | 2.5 | 1020 |
| 28 | 225.0 | 65.0 | 1275 |
| 35 | 150.0 | 10.0 | 750 |
| Percent Reduction Using Abbotts Formula | | | |
| 1 | 99.6 | | 99.4 |
| 7 | 99.2 | | 99.3 |
| 14 | 99.1 | | 99.5 |
| 21 | 97.5 | | 99.7 |
| 28 | 82.3 | | 94.9 |
| 35 | 66.6 | | 97.7 |

Example 6

The following formulation is useful as a rose bush cide spray.

| Ingredients | Percentage |
|---|---|
| DI Water | 97.846 |
| Pemulen TRI | .100 |
| Triethanol amine | .050 |
| Triflorine | .007 |
| Foraperle 303 | 2.000 |

The formulation extends the efficacy of the fungicide by extending the intervals between sprayings as compared to a formulation without the water proofing agent (fluorinated acrylic copolymer). It also prevents wash off and dilution of the fungicide.

Example 7

A herbicide spray concentrate was prepared as follows.

| Ingredients | Percentage |
|---|---|
| Water | 95.5 |
| Pemulen TRI | .5 |
| Isopropylamine salt of glyphosate | 2.0 |
| Foraperle 303 | 2.0 |

The concentrate is diluted with water before application to weeds. The presence of the fluorinated acrylic copolymer eliminates the need to retreat or reapply the herbicide formulation should it unexpectedly rain within about 6 to 24 hours from the time of applying the herbicide.

Example 8

Premis insecticidal sprays A and B, which resist water and oil were formulated as follows.

| | Ingredients | Percentage |
|---|---|---|
| A. | Water | 96.30 |
| | Pemulen TR2 | .15 |
| | Triethanol amine | .05 |

-continued

|   | Ingredients | Percentage |
|---|---|---|
|   | Resmethrin | .50 |
|   | Foraperle 303 | 3.00 |
| B. | Mineral spirits | 89.94 |
|   | Deltamethrin | .06 |
|   | Foraperle B208 | 10.00 |

The fluorinated acrylic copolymer (Foraperle) makes formulations A and B both hydrophobic and lipophobic. The above formulations when applied to various substrates such as wood, tile, concrete, carpet, linoleum and the like not only resist wash off and dilution of the active ingredient by water but also resist dilution of the active ingredient and its being rendered unavailable due to absorption in various oils and greases found in restaurants, kitchens, and the like.

Example 9

Anti-cribbing coating. Horses are known to bite into and chew on exposed wood such as fencing, gates, stalls, etc. A formulation to prevent such cribbing and which is very resistant to removal by water when subjected to rain or washing was made as follows.

| Extracts | A | B |
|---|---|---|
| Dried habanero pepper | 5.0 | 5.0 |
| Isopropyl alcohol | 95.0 | 47.5 |
| Distilled water | — | 47.5 |

The actives in the pepper were extracted by blending first in the alcohol and then in the case of B, adding the water. The extracts were then strained or filtered to remove solids.

|   | Percentages | |
|---|---|---|
| Ingredients | 1 | 2 |
| Extract A | 96.0 | — |
| Extract B | — | 96.0 |
| Foraperle 200 | 4.0 | — |
| Foraperle 333 | — | 4.0 |

Both formulations were found to be very effective in preventing horses from cribbing. The Foraperle fixed the actives found in the pepper and rendered the actives very water resistant. These formulations can be applied to vegetation such as trees and shrubs in order to prevent damage to the vegetation by browsing animals such as cattle, deer and rabbits. Other peppers that can be used include cajun and jalopeno peppers and extracts thereof.

Example 10

Since the loss of the use of chlorinated hydrocarbon pesticides, due to environmental issues, there has been a need for a safe residual termiticide. The discovery of being able to protect active ingredients with the fluorinated polymers makes such a product possible. The fluorinated polymers are very stable chemicals and pose no environmental threat. The combining of a readily biodegradable pesticide with a fluorinated polymer and applying that product to a wood substrate allows the pesticide to be fixed within the wood. The fluorinated polymer functions by making the pesticide and wood waterproof, thus preventing the water-pesticide association. This stops general chemical degradation reactions, such as hydrolysis, from taking place within the wood substrate. The fluorinated polymers also prevent the pesticide from being leached from the wood by being displaced by water and contributing to ground and water contamination. It is not precisely known how termites find their food other than random contact. The termite will, however, travel long distances under or above ground to reach a food source. This is demonstrated by a current method of testing utilized by USDA, wherein a wood two-by-four is driven into sterile ground, then a six foot circle of cement is poured around the two-by-four. Termites have the ability to locate the two-by-four in a very short time. One possibility for this phenomenon is that the termite picks up a chemical trail to direct itself to its food source. It could be projected that the chemicals that make the trail would transport themselves via the ground water. It is believed that the chemical-water interface could be prevented by use of the fluorinated polymers. The wood would in essence be camouflaged from the termite. Should, however, the termite randomly come in contact with the wood, low levels of protected pesticide would prevent the termite from breaking through the barrier or interface.

The following three formulas possess superior residual and efficacy as compared to the same formulations using the same actives and levels of actives but not including fluorinated polymers when applied to the wood substrate and dried.

|   | Percentages | | |
|---|---|---|---|
| Ingredients | 1 | 2 | 3 |
| Deltamethrin | .5 | — | — |
| Permethrin | — | 5.0 | 5.0 |
| Foraperle B208 | 10.0 | — | — |
| Foraperle 333 | — | — | 5.0 |
| Foraperle 303 | — | 5.0 | — |
| Aliphatic Solvent | 56.5 | — | — |
| Aromatic Solvent | 33.0 | — | — |
| Pemulen TR-2 | — | .2 | — |
| Triethanol Amine | — | .1 | — |
| Isopropyl Alcohol | — | 30.0 | 90.0 |
| Water | — | 56.7 | — |
| Epoxidized Soybean Oil | — | 3.0 | — |

Example 11

Antimicrobial/Fungicidal Wood Treatment

There has long been the need to preserve wood when placed into or next to the soil. As environmental issues come to bear on traditional methods of preservation, such as creosote, new methods are needed. The fluorinated polymer formulations of the present invention provide a means of fulfilling this need. The following two formulas offer outstanding wood preservation with excellent residual and efficacy properties.

|   | Percentages | |
|---|---|---|
| Ingredients | 1 | 2 |
| Isopropyl alcohol | 89.0 | 89.0 |
| Foraperle 200 | 10.0 | 10.0 |
| Phenol | 1.0 | — |
| Zinc methyldithiocarbamate | — | 1.0 |

Example 12

Antimicrobial/Fungicidal Treatment for Horse Hooves

| Ingredients | Percentage |
| --- | --- |
| Isopropyl Alcohol | 89.0 |
| Zinc Undecylenate | 1.0 |
| Foraperle 200 | 10.0 |

The above formula keeps the active ingredient on the hoof as well as the ankle of a horse even in wet, acid or alkaline soils.

Example 13

Eight Hour Waterproof Sun Screen

The following formula was subjected to SPF (Sun Protection Factor) testing before exposure to water and after exposure to a total of eight hours in a whirlpool with a circulating current. The results were a static SPF value of 35.83 and after eight hour extended immersion a value of 35.83.

| Ingredients | Percentages |
| --- | --- |
| Distilled Water | 61.5 |
| Carbopol 1342 | .2 |
| Emollient Ester | 10.0 |
| Octyl Methoxycinnamate | 7.5 |
| Oxybenzone | 5.0 |
| Octyl Salicylate | 5.0 |
| Octylcrylene | 4.0 |
| Preservative | .5 |
| Sorbitan Stearate | 4.0 |
| Vinylpyrrolidone Copolymer | 1.0 |
| Ammonium Hydroxide | .1 |
| Foraperle 303 | 1.0 |

Without any intention of being bound by theory, it is believed that the active ingredients in the several formulations described herein are made water and oil resistant by the fluorinated acrylic copolymers when applied to a substrate for the following reason. Due to the general insolubility of the fluorinated acrylic copolymer and its low surface tension, when it is exhausted from the formulation along with the active ingredient to a substrate, the fluorinated acrylic copolymer coalesces and covers or disperses with the active ingredient rendering it water and oil resistant. In accordance with the present invention, the time span over which the active ingredient is effective is lengthened even though the active ingredient after being applied to a target substrate is adversely and/or prematurely contacted with water or oil. These properties are very important economically and environmentally because it eliminates or very significantly reduces the need for re-application of the active ingredient and lengthens the time between applications of the active ingredient.

The addition of an effective amount of a fluorinated acrylic copolymer to any active ingredient containing liquid formulation imparts water and oil resistance to the active ingredient when it is applied to a substrate. The active ingredients of particular interest in liquid formulations include biologically active ingredients such as: insect and animal repellents; insect and animal attractants; insect and plant growth regulators; pesticides including insecticides, acaricides, parasiticides, herbicides and rodenticides; sunscreen agents; and medicines or pharmaceuticals for topical application. Specific examples within the foregoing active ingredients include: Stabilene, MGK 874, deet, MGK 326 and MGK 11; muscalure, disparlure, and trimedlure; glyphosine, norflurazon, methoprene, hyproprene and diflubenzuron; naturaland synthetic pyrethroids, carbamates, organophosphates, triforine, glyphosate, methazole, warfarin and bromethalin; and anti-inflammatory agents.

Among the fluorinated acrylic copolymers useful as the water and oil proofing agents in the present invention are those prepared by the polymerization of a perfluoralkyl acrylate of formula I and an acrylate of formula II using conventional procedures. Perfluoroalkyl acrylate monomers such as those of the formula

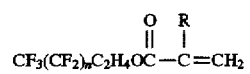

in which R is hydrogen or methyl and n is the positive integer 3 to 13 and mixtures thereof can be used to form a copolymer with an acrylate monomer II such as ethyl methacrylate, methyl methacrylate, ethyl acrylate, 2-hydroxyethyl methacrylate, and mixtures thereof. Additional suitable acrylic monomers for the fluorinated acrylic copolymers used in the present invention are described in U.S. Pat. Nos. 4,478,975 and 4,778,915, the disclosures of which are incorporated herein by reference.

The term "substrate", as used herein, is used broadly to include both animate and inanimate objects. Thus, it includes humans, large animals such as cows and horses, small animals such as dogs, cats, swine and sheep, vegetation such as weeds, trees and shrubs, surfaces such as wood, concrete, metal, tile, textiles, plastic, etc.

What is claimed is:

1. An active ingredient containing liquid formulation for depositing the active ingredient on a substrate when the formulation is applied to the substrate which consists essentially of:

an effective amount of an active ingredient;

a fluorinated acrylic copolymr in an amount effective to make said active ingredient resistant to removal or dilution by water or oil after deposition of the active ingredient onto said substrate; and a solvent selected from water, organic solvent or a mixture of water and organic solvent, said active ingredient being selected from the group consisting of insect and animal repellents, insect and animal attractants, insect and plant growth regulators, pesticides selected from the group consisting of insecticides, acaricides, herbicides and rodenticides, sunscreen agents and anti-inflammatory agents.

2. The formulation according to claim 1 wherein the active ingredient is a repellent.

3. The formulation according to claim 1 wherein the active ingredient is an insect repellent.

4. The formulation according to claim 3 wherein the substrate is a large animal.

5. The formulation according to claim 3 wherein the substrate is a small animal.

6. The formulation according to claim 1 wherein the active ingredient is a pesticide.

7. The formulation according to claim 6 wherein the pesticide is a herbicide.

8. The formulation according to claim 6 wherein the active ingredient is an insecticide.

9. The formulation according to claim 6 wherein the active ingredient is an insecticide and the substrate is a large animal.

10. The formulation according to claim 6 wherein the active ingredient is an insecticide and the substrate is a small animal.

11. The formulation according to claim 1 wherein the active ingredient is a sunscreen agent and the substrate is a human.

12. The formulation according to claim 1 wherein the fluorinated acrylic copolymer is formed from a fluorinated monomer of formula I and a monomer of formula II, said monomer of formula II being present in the amount of 1 to 30 percent, by weight, of the total weight of the monomers of formula I and II,

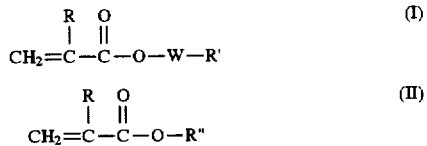

wherein R is hydrogen or a lower alkyl of 1 to 4 carbon atoms, W is an alkylene of 1 to 6 carbon atoms, R' is a perfluoroalkyl of 2 to 20 carbon atoms and R" is lower alkyl of 1 to 6 carbon atoms, hydroxyalkyl of 2 to 4 carbon atoms or the group —($CH_2$)n—NH—R'" in which R'" is lower alkyl of 1 to 6 carbon atoms or cycloalkyl and n is an integer of 2 to 4.

13. The formulation according to claim 12 wherein the copolymer is formed by emulsion polymerization.

14. The formulation according to claim 12 wherein the monomer of formula II is present in the amount of 5 to 25 percent.

15. The formulation according to claim 12 wherein R is hydrogen or methyl, W is an alkylene of 2 to 4 carbon atoms, R' is a perfluoroalkyl of 5 to 12 carbon atoms and R'" is lower alkyl.

16. The formulation according to claim 12 wherein R is methyl, W is alkylene of 2 carbon atoms, R' is a perfluoroalkyl of 5 carbon atoms and R" is methyl or ethyl.

17. The formulation according to claim 16 wherein the copolymer is formed by emulsion polymerization.

18. The formulation according to claim 17 wherein the monomer of formula II is present in the amount of 5 to 25 percent.

19. The formulation according to claim 1 wherein the solvent is water.

20. The formulation according to claim 2 wherein the repellent is an anti-cribbing agent and the substrate is wood.

* * * * *